United States Patent
Küllmer

(10) Patent No.: US 6,684,481 B2
(45) Date of Patent: Feb. 3, 2004

(54) METHOD OF PRODUCING A SURGICAL SAW BLADE

(75) Inventor: Michael Küllmer, Lemgo (DE)

(73) Assignee: Gebr. Brasseler GmbH & Co. KG, Lemgo (DE)

(*) Notice: Subject to any disclaimer, the term of this patent is extended or adjusted under 35 U.S.C. 154(b) by 131 days.

(21) Appl. No.: 10/098,072

(22) Filed: Mar. 14, 2002

(65) Prior Publication Data
US 2002/0133186 A1 Sep. 19, 2002

(30) Foreign Application Priority Data
Mar. 14, 2001 (DE) .......................... 101 12 286

(51) Int. Cl.$^7$ ............................... B23P 13/04
(52) U.S. Cl. .................. 29/558; 29/412; 606/82; 606/178; 76/104.1
(58) Field of Search .................. 29/557, 558, 412, 29/417; 606/82, 178; 76/104.1

(56) References Cited

U.S. PATENT DOCUMENTS

| 4,036,236 A | | 7/1977 | Rhodes, Jr. |
| 4,584,999 A | | 4/1986 | Arnegger |
| 4,637,391 A | * | 1/1987 | Schlein ........................ 606/178 |
| 4,986,826 A | * | 1/1991 | Roger .......................... 606/82 |
| 5,306,285 A | * | 4/1994 | Miller et al. .................. 606/178 |
| 5,317,938 A | * | 6/1994 | de Juan et al. ............. 76/104.1 |
| 5,569,257 A | * | 10/1996 | Arnegger et al. ............. 606/82 |
| 5,842,387 A | * | 12/1998 | Marcus et al. ............. 76/104.1 |
| 5,897,558 A | * | 4/1999 | Frieze et al. .................. 606/82 |
| 6,253,442 B1 | * | 7/2001 | Benson et al. ................. 29/557 |
| 6,327,772 B1 | * | 12/2001 | Zadno-Azizi et al. ......... 29/557 |
| 6,353,204 B1 | * | 3/2002 | Spaay et al. ............. 219/121.72 |
| 6,615,496 B1 | * | 9/2003 | Fleming et al. ............. 76/104.1 |
| 2002/0078576 A1 | * | 6/2002 | Carr et al. ..................... 30/357 |
| 2003/0032971 A1 | * | 2/2003 | Hausmann et al. ......... 606/178 |

FOREIGN PATENT DOCUMENTS

| DE | 3222339 A1 | 1/1983 |
| DE | 19804762 A1 | 7/1999 |
| DE | 100 10 526 A 1 | 10/2001 |
| EP | 0 695 607 A1 | 2/1996 |
| GB | 2 103 148 A | 2/1983 |

* cited by examiner

Primary Examiner—David P. Bryant
(74) Attorney, Agent, or Firm—Thompson Coburn LLP

(57) ABSTRACT

The present invention relates to a method of producing a surgical saw blade comprising a clamping portion and a working area provided with a toothing, wherein the clamping portion and the working area are produced by means of an etching method and the toothing is subsequently cut by means of a laser type cutting method.

20 Claims, 2 Drawing Sheets

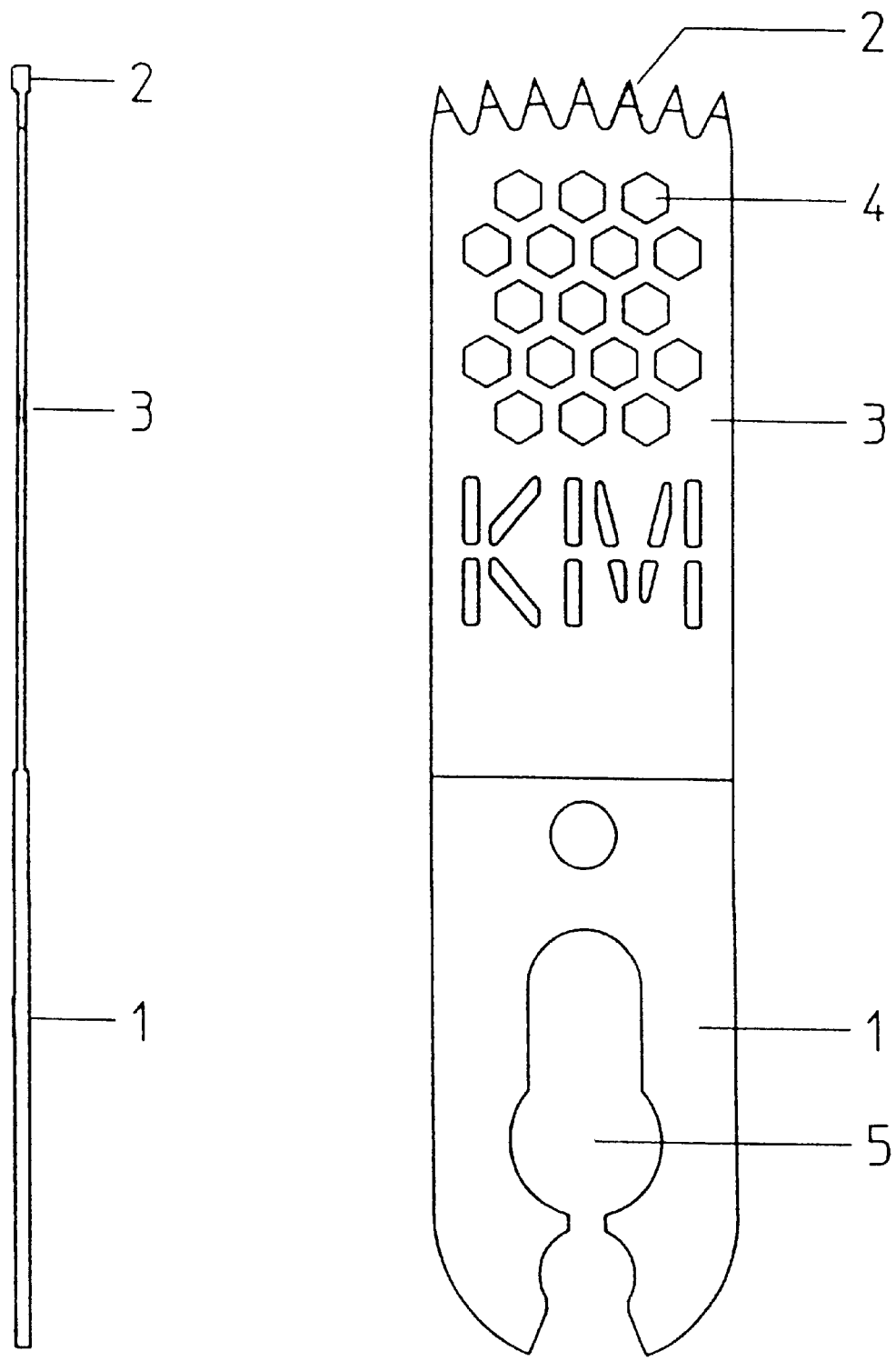

METHOD OF PRODUCING A SURGICAL SAW BLADE

BACKGROUND OF THE INVENTION

The present invention relates to a method of producing a surgical saw blade comprising a clamping portion and a working area provided with a toothing.

Surgical saw blades of the described type are known from the prior art in many different designs. They are mounted on drive units by which they are induced to perform an oscillating reciprocating movement. In this process the toothing portion which is shaped in the form of a circular arc is moved accordingly, whereby a cutting operation is made possible. The sawing or cutting operation may be performed by manual guiding; alternatively, it is also possible to use the surgical saw blade by means of a template to ensure a precise guidance of the cutting operation. Saw blades of the described type are typically made from thin steel of high strength, the thickness being in orders ranging from approximately 0.7 to 0.2 mm.

BRIEF SUMMARY OF THE INVENTION

It is the object of the present invention to provide a method of producing a surgical saw blade which, while being of a simple design and easy to use, can be carried out at low costs and also permits the production of high-precision saw blades.

According to the invention this object is achieved by the features of the main independent claim; the dependent claims show further advantageous developments of the invention.

Thus, according to the invention the clamping portion and the working area are produced by means of an etching method and the toothing is then cut by means of a laser type cutting method.

The saw blade according to the invention is characterized by a number of considerable advantages.

Thanks to the use of a shape etching method, it is possible to produce the outer contour of the saw blades rapidly and above all at low costs and to achieve the necessary precision. When the toothing is produced, an etching method is of no advantage because an etching method will always leave rounded or at least slightly rounded edges. This is not useful for sharp cutting edges. With the laser type cutting method according to the invention, it is thus possible to produce the toothing itself in a precise way in such a manner that sharp cutting edges are obtained. An after-treatment or grinding of the toothing is thus not required.

In a particularly advantageous development of the invention, the toothing is prefabricated by means of the etching method with a tolerance and finished with the laser type cutting method. The amount of material to be removed by the laser type cutting method can thus be minimized considerably.

Normally, recesses are formed in surgical saw blades in the clamping portion to permit an attachment to a drive unit. According to the invention, these recesses, like the recesses in the working area, can be produced by means of the etching method in a particularly simple and inexpensive manner. In particular, this is possible in the same working steps as the formation of the outer contour.

A further advantage of the procedure according to the invention is that different thickness ranges of the clamping portion and/or of the working area can be produced by means of the etching method. For instance, it is possible to keep the thickness of the clamping portion unchanged, as compared to the starting material, while the working area may have a reduced thickness. It is particularly advantageous when the toothing has a larger thickness than the working area, in particular in the area of the tooth tips of the toothing. The cutting performance is thereby enhanced. On the other hand, the mechanical strength of the toothing itself is increased.

According to the invention the saw blade is preferably made from surgical steel; in particular, martensitic steels or austenitic steels having a strength of greater than 1000 N/mm$^2$ may be used and can be hardened to the necessary hardness or have a corresponding basic hardness.

BRIEF DESCRIPTION OF THE SEVERAL VIEWS OF THE DRAWINGS

The accompanying drawings, which are incorporated in and form a part of the specification, illustrate the embodiments of the present invention and together with the description, serve to explain the principles of the invention. In the figures, like parts are provided with like reference numerals. In the drawings:

FIG. 3 is a top plan view, analogous to FIG. 1, of a further embodiment of the saw blade according to the invention; and FIG. 4 is a side view of the saw blade shown in FIG. 3.

DETAILED DESCRIPTION OF THE INVENTION

Figures 1, 2:
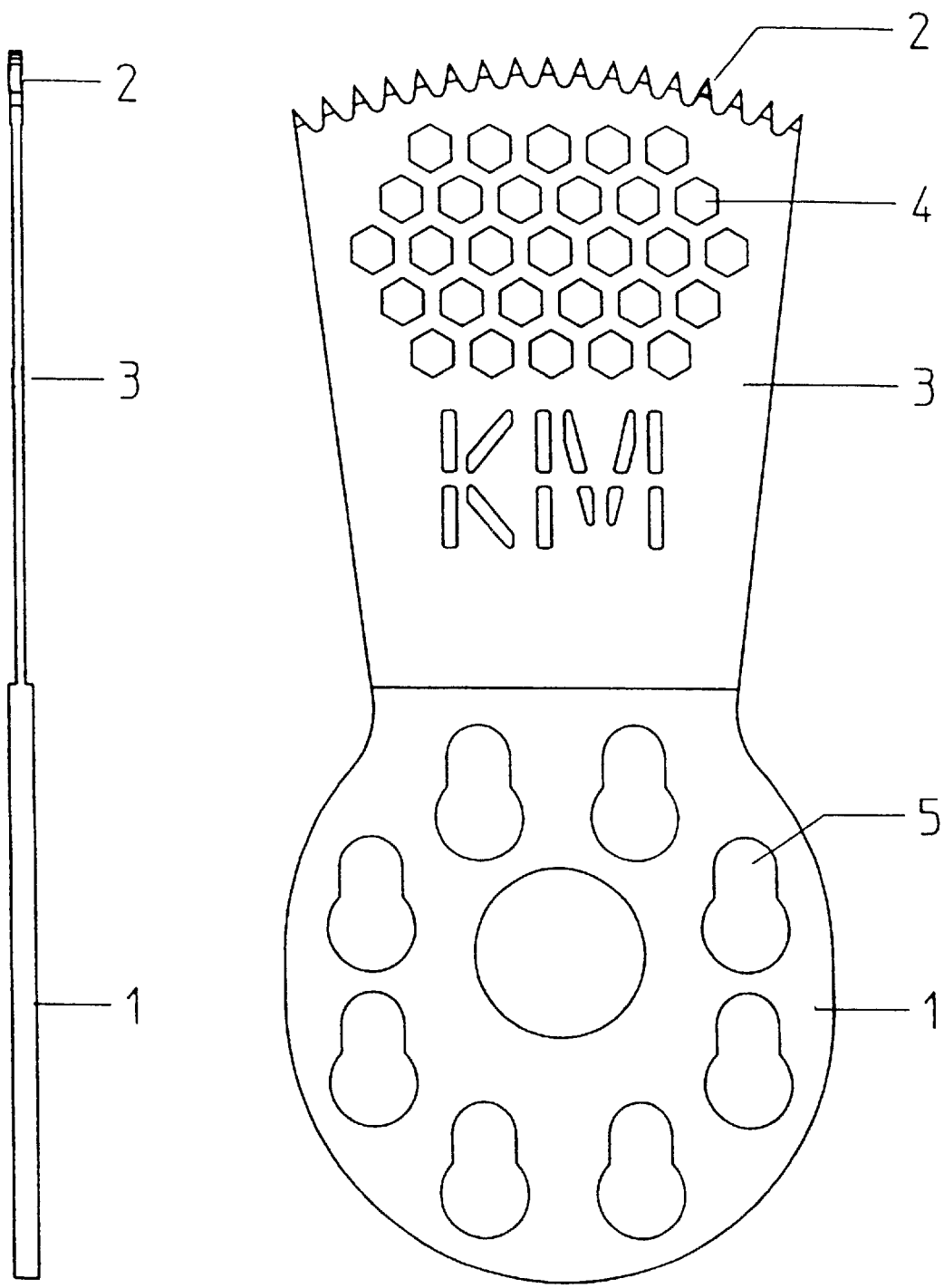
FIG. 1 is a top plan view of a first embodiment of the saw blade according to the invention.
FIG. 2 is a side view of the saw blade shown in FIG. 1.

As becomes apparent from the figures, the saw blade comprises a clamping portion 1 which is provided with at least one recess 5 which serves clamping and supporting purposes in a drive unit (not shown). Since the drive units and the supporting possibilities correspond to those well known in the art, a detailed description is omitted.

The clamping portion is followed by a working area 3 whose front end is provided with a toothing 2. The toothing 2 is arranged in the manner of an arc, the center point of the arc coinciding with the pivotal center point of the saw blade mounted in the drive unit.

Each of the side views of FIGS. 2 and 4 shows that the saw blades may have a different thickness. In the embodiment of FIGS. 1 and 2, for instance, the clamping portion may have a thickness of approximately 0.5 mm while the working area may be provided with a thickness of approximately 0.27 mm. The toothing 2, in turn, may have a thickness of approximately 0.35 mm. On the whole, the saw blade has a length of approximately 35 mm, and it has a diameter of approximately 16 mm on its clamping portion while the toothing has a width of approximately 15 mm. As follows further from FIGS. 1 and 2, additional recesses 4 may preferably be provided within the working area 3 to permit a look at the sawing portion during the working operation.

The embodiment as illustrated in FIGS. 3 and 4 shows a small elongated saw blade. Like parts are designated by like reference numerals as in the preceding embodiment. In such embodiment, the saw blade may have a total length of approximately 34 mm and a width of approximately 8 mm. The thickness of the clamping portion may be approximately 0.38 mm. The toothing may have the same thickness as that of the clamping portion, while the working area 3 has a thickness of approximately 0.2 mm.

The thickness of the working area 3 can be reduced by means of the shape etching method according to the invention.

In view of the foregoing, it will be seen that the several advantages of the invention are achieved and attained. The embodiments were chosen and described in order to best explain the principles of the invention and its practical application to thereby enable others skilled in the art to best utilize the invention in various embodiments and with various modifications as are suited to the particular use contemplated. As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

I claim:

1. A method of producing a surgical saw blade having a clamping portion and a working area provided with a toothing, comprising the steps of:

shape etching said clamping portion and said working area from a starting material;

laser cutting said toothing in said working area.

2. The method according to claim 1, further comprising prefabricating said toothing with a tolerance by etching prior to the toothing being cut.

3. The method according to claim 2, further comprising etching one or more recesses in at least one of said clamping portion and said working area.

4. The method according to claim 2, wherein said etching provides for different thickness ranges of at least one of said clamping portion and said working area.

5. The method according to claim 4, wherein said clamping portion has a larger thickness than said working area and said toothing has a larger thickness than said working area.

6. The method according to claim 2, wherein said starting material is surgical steel.

7. The method according to claim 1 or 2, wherein said toothing, once cut, is ready for use.

8. The method according to claim 7, further comprising etching one or more recesses in at least one of said clamping portion and said working area.

9. The method according to claim 7, wherein said etching provides for different thickness ranges of at least one of said clamping portion said working area.

10. The method according to claim 9, wherein said clamping portion has a larger thickness than said working area and said toothing has a larger thickness than said working area.

11. The method according to claim 7, wherein said starting material is surgical steel.

12. The method according to claim 1, further comprising etching one or more recesses in at least one of said clamping portion and said working area.

13. The method according to claim 12, wherein said etching provides for different thickness ranges of at least one of said clamping portion and said working area.

14. The method according to claim 13, wherein said clamping portion has a larger thickness than said working area and said toothing has a larger thickness than said working area.

15. The method according to claim 12, wherein said starting material is surgical steel.

16. The method according to claim 1, wherein said etching provides for different thickness ranges of at least one of said clamping portion and said working area.

17. The method according to claim 16, wherein said starting material is surgical steel.

18. The method according to claim 16, wherein said clamping portion has a larger thickness than said working area and said toothing has a larger thickness than said working area.

19. The method according to claim 18, wherein said starting material is surgical steel.

20. The method according to claim 1, wherein said starting material is surgical steel.

* * * * *